United States Patent

Wu et al.

[11] Patent Number: 5,414,184
[45] Date of Patent: May 9, 1995

[54] ALKANE DISPROPORTIONATION

[75] Inventors: An-hsiang Wu; Bruce B. Randolph; Marvin M. Johnson, all of Bartlesville, Okla.

[73] Assignee: Phillips Petroleum Company, Bartlesville, Okla.

[21] Appl. No.: 178,683

[22] Filed: Jan. 10, 1994

[51] Int. Cl.6 .................................. C07C 6/08
[52] U.S. Cl. ..................... 585/708; 585/752
[58] Field of Search .................. 585/708, 752

[56] References Cited

U.S. PATENT DOCUMENTS

| | | | |
|---|---|---|---|
| 5,245,103 | 9/1993 | Wu | 585/743 |
| 5,245,794 | 10/1993 | Wu | 585/741 |
| 5,294,578 | 3/1994 | Ho et al. | 502/62 |

OTHER PUBLICATIONS

J. P. Franck and J. F. Le Page, "Ethyl Aluminum Chlorides Anchored on Platinum-Impregnated Alumina as Hyperacid Catalyst for Isomerization of Light Alkanes", 7th International Congress on Catalysis, 1981, pp. 1018–1030.

A. Krzywicki and M. Marczewski, "Superacidity of Modified Gamma-Alumina", Journal Chem. Society, Faraday I, 1980, pp. 1311–1323.

*Primary Examiner*—P. Achutamurthy
*Attorney, Agent, or Firm*—K. K. Brandes

[57] ABSTRACT

$C_4$–$C_{15}$ alkanes (preferably $C_4$–$C_8$ alkanes) are disproportionated in the presence of at least one alkylaluminum chloride (preferably isobutylaluminum dichloride), at least one chloroalkane (preferably carbon tetrachloride), and at least one solid material (selected from a group comprising alumina, silica, aluminosilicates, various other aluminum compounds, various boron compounds, and sulfonated styrene polymers).

20 Claims, 1 Drawing Sheet

ALKANE DISPROPORTIONATION

BACKGROUND OF THE INVENTION

Low-boiling alkanes (such as butanes and pentanes) are components of gasoline fuels. Recent governmental regulations mandate that the vapor pressure of gasoline fuels be lowered. Consequently, the content of these low-boiling alkanes in gasoline will have to be reduced. The present invention is directed to a process for converting a portion of these low-boiling alkanes to higher-boiling alkanes which are environmentally more acceptable as motor fuel components.

SUMMARY OF THE INVENTION

It is an object of this invention to partially disproportionate alkanes to higher-boiling and lower boiling alkanes. Other objects and advantages will become apparent from the detailed description of the invention and the appended claims.

In accordance with this invention, an alkane conversion process comprises the steps of:

(1) mixing a liquid feed which comprises at least one feed alkane containing 4–15 carbon atoms per molecule with at least one alkylaluminum chloride and at least one chloroalkane, (2) contacting the mixture obtained in step (1) with a solid material selected from the group consisting of alumina, silica, silica-alumina, aluminosilicates (clays, zeolites), titania ($TiO_2$), zirconia ($ZrO_2$), hafnia ($HfO_2$), aluminum phosphate, aluminum oxide/phosphate, aluminum borate, aluminum oxide/borate, aluminum sulfate, aluminum oxide/sulfate, boron oxide, boron phosphate, boron oxide/phosphate, boron sulfate, boron oxide/sulfate, sulfonated ion-exchange resins (in particular, sulfonated styrene polymers) and mixtures thereof, at effective disproportionation conditions so as to produce a product having a lower concentration of feed alkane(s), a higher concentration of product alkanes containing more carbon atoms per molecule than the feed alkane(s), and a higher concentration of product alkanes containing fewer carbon atoms per molecule than the feed alkane(s); and (3) recovering the product alkanes from the reaction mixture of step (2).

Preferably, the feed alkane is normal-pentane, the alkylaluminum chloride is isobutylaluminum dichloride, and the chloroalkane (i.e., chlorine derivative of alkane) is carbon tetrachloride. In step (2), the solid material is generally contained in a fixed bed through which the mixture obtained in step (1) is passed. Unconverted feed alkane(s), the alkylaluminum chloride(s) and the chloroalkane(s) are generally separated from the product alkanes, and are recycled to step (1).

DETAILED DESCRIPTION OF THE INVENTION

Figure 1:
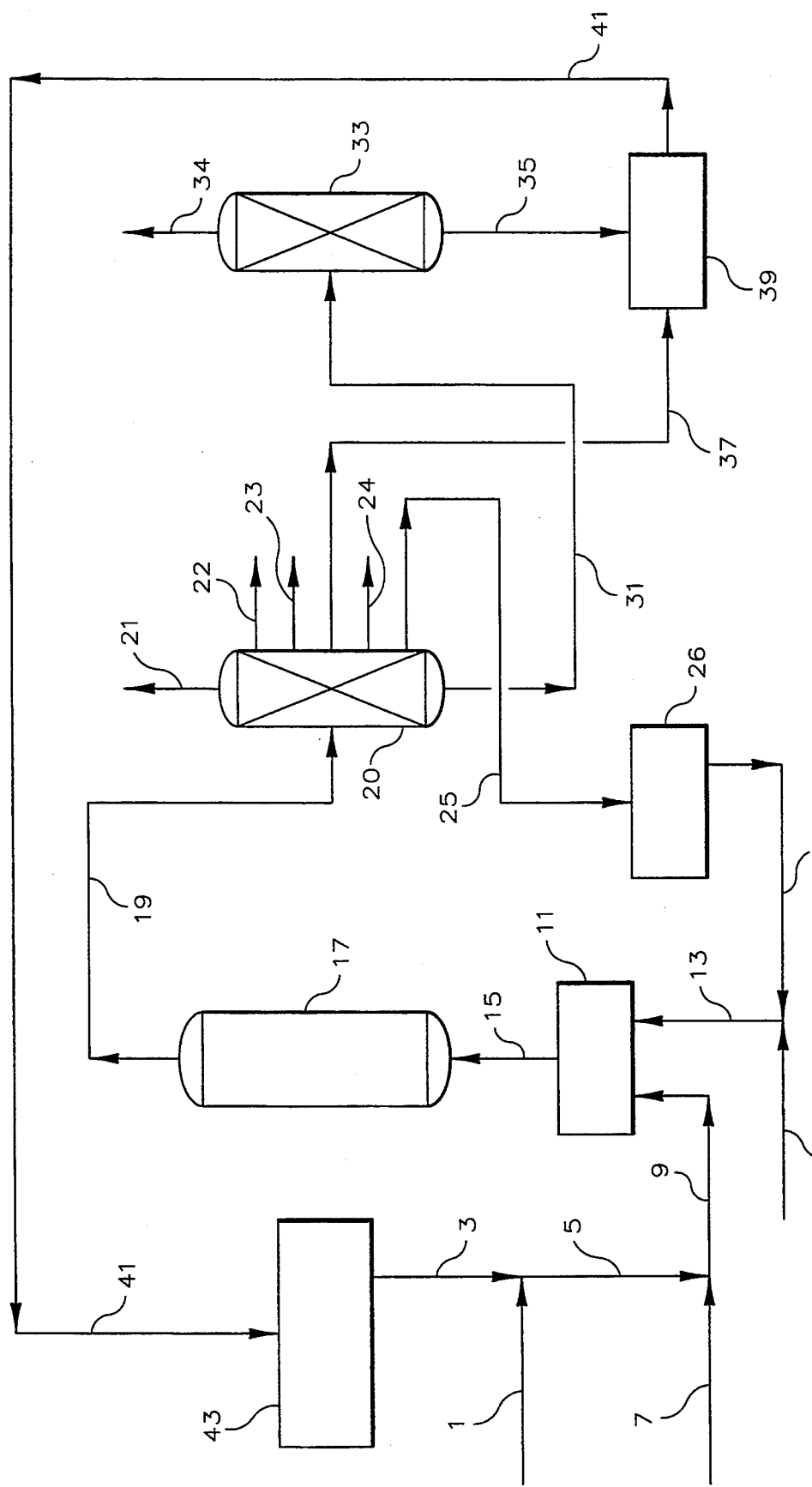
FIG. 1 illustrates the continuous conversion of normal-pentane in accordance with this invention.

Step (1) of the process of this invention can be carried out in any suitable manner. The feed alkane(s), the alkylaluminum chloride(s) and the chloroalkane(s) can be mixed with one another in any order. Generally, at least one feed alkane and at least one alkylaluminum chloride are first combined in a first solution, and then at least one chloroalkane is added to the first solution to form a second solution, which is then contacted with the solid material in step (2).

Suitable feed alkanes generally contain 4–15 carbon atoms per molecule, preferably 4–8 carbon atoms per molecule. These alkanes can be straight-chain alkanes (normal alkanes) or branched alkanes (isoalkanes). Non-limiting examples of preferred alkanes include (but are not limited to) n-butane, isobutane, n-pentane, isopentane (i.e., 2-methylbutane), n-hexane, isohexanes (such as 2-methylpentane, 3-methylpentane, 2,2-dimethylbutane), n-heptane, isoheptanes (such as methyl-substituted hexanes and dimethyl-substituted pentanes), n-octane, isooctanes (such as methyl-substituted heptanes, dimethyl-substituted hexanes), n-nonane, isononanes (in particular methyl-substituted octanes, dimethyl-substituted heptanes, trimethyl-substituted hexanes), n-decane and isodecanes (in particular methyl-substituted nonanes, dimethyl-substituted octanes, trimethyl-substituted heptanes, tetramethyl-substituted hexanes), normal and branched undecanes, normal and branched dodecanes, and the like, and mixtures thereof.

Generally the alkylaluminum chloride has the general formula of $R_xAlCl_{3-x}$, wherein x is 1 or 2, preferably 1, and each R is independently selected from the group consisting of alkyl radicals consisting of methyl, ethyl, n-propyl, isopropyl, n-butyl, isobutyl (2-methylpropyl), t-butyl (1,1-dimethylethyl), n-pentyl, branched pentyl radicals, and the like. The presently preferred alkylaluminum chloride is isobutylaluminum dichloride. Many of the alkylaluminum chloride compounds are commercially available. The preparation of the presently preferred alkylaluminum compound is described in Example I.

Generally, the chloroalkane contains 1–4 (preferably 3–4) chlorine atoms and 1–4 (preferably 1–2) carbon atoms per molecule. Non-limiting examples of preferred chloroalkanes include (but are not limited to) dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane. Presently preferred is carbon tetrachloride.

Suitable solid catalyst components have been described above. Preferred solid catalyst components include alumina (more preferably gamma-alumina), silica, silica-alumina (more preferably having a $SiO_2$:$Al_2O_3$ weight ratio of about 0.2:1 to about 1.5:1), clays, zeolites, aluminum phosphate, aluminum oxide/phosphate (more prefer;ably having an atomic Al:P ratio of about 0.1:1 to about 10:1), aluminum borate, aluminum oxide/borate (more preferably having an atomic Al:B ratio of about 0.1:1 to about 10:1), aluminum sulfate, aluminum oxide/sulfate (more preferably having an atomic Al:S ratio of about 0.1:1 to about 10:1), sulfonated styrene-divinylbenzene copolymer (more preferably containing 2–50 weight-% divinylbenzene) and mixtures thereof. Presently preferred solid catalyst components are described in Example I. Most of these solids-materials are commercially available. The preparation of others, such as aluminum oxide/phosphate and aluminum oxide/sulfate, is described in U.S. Pat. Nos. 5,254,794 and 5,233,119. The preparation of aluminum oxide/borate is described in an article by M. C. Tsai et al in Catalysis Letters 6 (1990), page 226. Generally, the surface area of these solid materials is in the range of about 200 to about 400 $m^2$/g (determined by the BET method of Brunauer, Emmett and Teller employing $N_2$). Preferably, the solids have a particle size in the range of about 0.4 mm to about 3.2 mm (i.e., smaller than about 6 mesh and larger than about 40 mesh).

Any effective concentration of the alkylaluminum chloride and of the chloroalkane in the alkane feed can be utilized. Generally, the concentration of each of these catalyst components in the feed is about 2–6 weight-%. Any effective weight ratio of the alkylaluminum chloride component to the chloroalkane (both present as soluble catalyst components in the liquid feed) can be employed. Preferably, the weight ratio of the alkylaluminum chloride component to the chloroalkane component (after both have been added to the feed) is about 0.5:1 to about 3:1.

Any effective ratio of the combined weight of the alkylaluminum chloride and the chloroalkane components (both dissolved in the feed) to the solid catalyst component can be employed in batch processes. Generally, this ratio is about 1.2:1 to about 2:1. In continuous processes, an effective ratio of the three catalyst components is attained by selecting a concentration of about 2–6 weight-% of each soluble catalyst component (i.e., alkylaluminum chloride and chloroalkane) in the liquid feed and a liquid hourly space velocity of the feed in the range of about 1 to about 10 cc liquid feed per cc solid per hour.

The process of this invention for converting $C_4$–$C_{15}$ feed alkanes to other alkanes can be carried out under any suitable reaction conditions at a relatively low temperature of up to about 100° C., more preferably about 20°–50° C. (most preferably about 30°–40° C.), generally at about 1–5 atm. pressure. The feed alkane(s) can be contacted with the catalyst composition in any suitable mode, such as in a slurry-type operation in which the catalyst components are dispersed in the feed alkane(s), or in a moving catalyst bed operation wherein feed and catalyst components move in the same direction, or in a fixed catalyst bed operation (preferred) in which the alkane feed which contains dissolved alkylaluminum chloride catalyst component and the chloroalkane catalyst component flows either upward or downward through a solid catalyst layer (or several catalyst layers). The time of contact between the feed alkane(s) and the three catalyst components generally is in the range of about 5 minutes to about 10 hours, preferably about 1–3 hours. The conversion process can be carried out as a batch operation or as a continuous operation, The process of this invention generates a multitude of products, as is demonstrated in the examples. Thus, it is necessary to separate the various formed hydrocarbon products from one another, from unconverted feed hydrocarbon(s), and from dissolved catalyst components. This separation can be carried out in any suitable manner, generally by fractional distillation, as is easily determined by persons familiar with liquid-liquid separation technologies. A preferred separation scheme, including the recycle of two catalyst components and of unconverted feed alkane, is illustrated in FIG. 1 and described in Example IV.

The following examples are provided to further illustrate the processes of this invention, and are not to be construed as unduly limiting the scope of this invention.

Example I

This example illustrates the disproportionation of n-pentane in the presence of a catalyst system which comprises two components which are soluble in the n-pentane feed and a third component which is solid, in accordance with this invention.

A mixture of 4.418 g (25 millimoles) diisobutylaluminum chloride and 3.333 g (25 millimoles) aluminum chloride were dissolved in 147.25 g (235 mL) of dry n-pentane. The solution was stirred at room temperature under a dry nitrogen atmosphere for about 24 hours. The two dissolved aluminum compounds reacted with one another, and a 5 weight-% solution of isobutylaluminum dichloride was formed.

0.2 mL (0.32 g) of carbon tetrachloride was then added to 10 mL of the above-described isobutylaluminum dichloride/n-pentane solution. Also added to the above-described solution was 0.50 gram of one of various solid materials. Generally, the particle size of the added solid materials was 18–40 mesh. The following solid materials (some of which are described in U.S. Pat. Nos. 5,254,794) were employed:

Solid A was an activated carbon having a BET/$N_2$ surface area of 1400 $m^2$/g.

Solid B1 was a gamma-alumina having a surface area of about 180 $m^2$/g and a pore volume of 1.02 cc/g; marketed by American Cyanamid Company, Deerfield, Ill.

Solids B2–B5 were also alumina materials which were similar to solid B1 but had been provided by different manufacturers.

Solid C1 was a silica which had been calcined at about 600° C. for about 3 hours and had a surface area of about 340 $m^2$/g; marketed by the Davison Catalyst Division of W. R. Grace and Company, Baltimore, under the product designation of G-57.

Solid C2 was another silica, marketed by the Davison Catalyst Division under the product designation of G-62.

Solid D1 was a silica-alumina containing 50 weight-% of each component, having a surface area of 300–330 $m^2$/g, prepared by coprecipitating hydrated silica and hydrated alumina from an aqueous solution, followed by calcining at about 600° C. for about 2 hours.

Solids D2 and D3 were silica-aluminas containing 25 weight-% silica and 75 weight-% alumina, having been prepared by the method described for Solid D1 (except that the concentrations of the Al and Si compounds in the solution were different).

Solid E was an aluminum oxide/phosphate material which had been prepared by adding enough of a concentrated aqueous ammonia solution to an aqueous solution of $Al(NO_3)_3$ and $NH_4H_2PO_4$, having a $PO_4$:Al molar ratio of about 0.5:1, so as to make the latter solution basic (i.e., to raise the pH to above 7) and to coprecipitate aluminum phosphate/hydroxide, followed by aging the coprecipitate under the basic solution for 1–2 hours at room temperature, filtering the aqueous slurry, drying the filter cake, and calcining it in air for about 3 hours at 600° C.

Solid F was an aluminum oxide/borate material which had been prepared substantially in accordance with the procedure for Solid E, except that $H_3BO_3$ was used in lieu of $NH_4H_2PO_4$. The $BO_3$:Al molar ratio was about 0.5:1.

Solid G was an aluminum oxide/sulfate material which had been prepared substantially in accordance with the procedure for Solid E, except that $(NH_4)_2SO_4$ was used in lieu of $NH_4H_2PO_4$. The $SO_4$:Al molar ratio was about 0.3:1.

Solid H was an acid-treated montmorillonite clay, marketed by Engelhard Corporation, Edison, N.J., under the product designation of Filtrol 71.

Solid I was a Y-zeolite (provided by Union Carbide Corporation, Danbury, Conn., under the product designation of LZ-Y62) which had been acid-treated and air calcined at 450° C.

Solid J was an acid-treated mordenite (a natural zeolite), which had been air-calcined at 450° C.

Solid K was a sulfonated styrene-vinylbenzene copolymer ion-exchange resin, having a surface area of 40–50 m²/g; marketed by Rohm and Haas, Philadelphia, Pa., and under the product designation of Amberlyst®15.

About 10 mL (6.6 g) of the above-described liquid mixture containing n-pentane, isobutylaluminum dichloride (also referred to as 2-methylpropylaluminum dichloride) and carbon tetrachloride (with the exception of control runs which excluded $CCl_4$) and each of the above-described solids (with the exception of another control run) were placed in a sealed glass flask and slightly agitated, at a temperature of about 40° C. and atmospheric pressure conditions, for 1–3 hours. Thereafter, the flask content was analyzed by means of a gas chromatograph. Pertinent test results are summarized in Table I.

TABLE I

| Catalyst Content in Feed | | | Wt. of Solid (g) | Reaction Time (Hr.) | n-Pentane Conversion (%) | % Selectivity[1] to | | |
|---|---|---|---|---|---|---|---|---|
| Wt-% iBuAlCl₂ | Wt-% CCl₄ | Solid | | | | $C_4$[2] | $C_6+$[3] | Isopentane |
| 4.7 | 4.8 | None | 0 | 2 | 2.9 | — | — | — |
| " | " | " | " | 3 | 2.2 | — | — | — |
| " | " | A | 0.50 | 2 | 7.4 | — | — | — |
| " | " | " | " | 3 | 7.8 | — | — | — |
| " | 0 | B1 | 0.50 | 1 | 1.4 | — | — | — |
| " | 4.8 | " | " | " | 54.2 | 29.6 | 32.4 | 38.0 |
| " | " | " | " | 2 | 64.8 | 34.1 | 31.1 | 34.8 |
| " | " | " | " | " | 64.9 | 17.4 | 50.5 | 32.0 |
| " | " | " | " | 3 | 67.7 | 21.7 | 44.1 | 34.2 |
| " | 0 | B2 | 0.50 | 1 | 2.1 | — | — | — |
| " | 4.8 | " | " | " | 58.0 | 32.4 | 26.2 | 41.3 |
| " | " | " | " | 2 | 71.8 | 34.1 | 33.2 | 32.7 |
| " | 0 | B3 | 0.50 | 1 | 2.3 | — | — | — |
| " | 4.8 | " | " | 1 | 38.0 | 18.1 | 41.2 | 40.7 |
| " | " | " | " | 2 | 48.3 | 21.4 | 42.0 | 36.6 |
| 4.7 | 0 | B4 | 0.50 | 1 | 3.4 | — | — | — |
| " | 4.8 | " | " | 1 | 49.0 | 26.2 | 33.7 | 40.0 |
| " | " | " | " | 2 | 56.1 | 20.9 | 43.7 | 35.4 |
| 4.7 | 0 | B5 | 0.50 | 1 | 1.9 | — | — | — |
| " | 4.8 | " | " | 1 | 71.4 | 25.9 | 39.8 | 34.2 |
| " | " | " | " | 2 | 77.8 | 28.8 | 40.6 | 30.7 |
| 4.7 | 0 | C1 | 0.50 | 1 | 8.2 | — | — | — |
| " | 4.8 | " | " | " | 57.3 | 15.2 | 58.8 | 26.0 |
| " | " | " | " | 2 | 58.7 | 29.8 | 39.5 | 30.7 |
| 4.7 | 0 | C2 | 0.50 | 1 | 2.0 | — | — | — |
| " | 4.8 | " | " | " | 74.3 | 5.4 | 82.7 | 11.9 |
| " | " | " | " | 2 | 68.7 | 39.7 | 27.9 | 32.3 |
| 4.7 | 0 | D1 | 0.50 | 1 | 9.2 | — | — | — |
| " | 4.8 | " | " | " | 68.8 | 25.0 | 39.9 | 35.1 |
| " | " | " | " | 2 | 78.6 | 25.8 | 49.8 | 24.4 |
| 4.7 | 0 | D2 | 0.50 | 1 | 2.2 | — | — | — |
| " | 4.8 | " | " | " | 77.4 | 6.6 | 76.6 | 16.8 |
| " | " | " | " | 2 | 69.1 | 43.2 | 17.6 | 39.2 |
| 4.7 | 0 | D3 | 0.50 | 1 | 1.6 | — | — | — |
| " | 4.8 | " | " | 1 | 64.8 | 39.2 | 27.2 | 33.6 |
| " | " | " | " | 2 | 68.8 | 43.3 | 22.6 | 34.1 |
| 4.7 | 0 | E | 0.50 | 1 | 1.4 | — | — | — |
| " | 4.8 | " | " | " | 81.9 | 12.7 | 69.5 | 17.8 |
| " | " | " | " | 2 | 77.0 | 28.9 | 36.5 | 34.6 |
| 4.7 | 0 | F | 0.50 | 1 | 1.8 | — | — | — |
| " | 4.8 | " | " | " | 58.8 | 11.3 | 68.2 | 20.5 |
| " | " | " | " | 2 | 54.8 | 14.2 | 54.9 | 30.9 |
| 4.7 | 0 | G | 0.50 | 1 | 3.9 | — | — | — |
| " | 4.8 | " | " | " | 43.6 | 21.8 | 41.7 | 36.5 |
| " | " | " | " | 2 | 40.1 | 20.8 | 32.0 | 47.2 |
| 4.7 | 0 | H | 0.50 | 1 | 4.3 | — | — | — |
| " | 4.8 | " | " | 1 | 63.1 | 27.7 | 33.9 | 38.4 |
| " | " | " | " | 2 | 73.1 | 26.7 | 39.7 | 33.6 |
| 4.7 | 0 | I | 0.50 | 1 | 2.8 | — | — | — |
| " | 4.8 | " | " | 1 | 27.4 | 29.1 | 31.4 | 39.5 |
| " | " | " | " | 2 | 44.6 | 30.6 | 31.5 | 37.9 |
| 4.7 | 0 | J | 0.50 | 1 | 2.6 | — | — | — |
| " | 4.8 | " | " | 1 | 14.8 | 29.6 | 30.8 | 39.5 |
| " | " | " | " | 2 | 51.2 | 26.8 | 31.9 | 41.2 |
| 4.7 | 0 | K | 0.50 | 1 | 2.4 | — | — | — |
| " | 4.8 | " | " | 1 | 40.3 | 32.8 | 27.0 | 40.2 |
| " | " | " | " | 2 | 45.6 | 34.1 | 27.9 | 38.0 |

[1]%-selectivity = yield of a product divided by n-pentane conversion times 100
[2]$C_4$ = n-butane alkanes and isobutane
[3]$C_7+$ = alkanes containing 6 or more than 6 carbon atoms per molecule Test data in Table I clearly show that a specific solid and a chloroalkane (specifically $CCl_4$) must be present as catalyst components during the n-pentane conversion reaction to result in a significant feed conversion. Activated carbon (Solid A) was not adequately effective as a solid catalyst component. The test data also show that the combined selectivity to disproportionation products ($C_4$ and $C_6+$ hydrocarbons) exceeded the selectivity to isopentane which was formed by the rival isomerization of n-pentane. Thus, the process of this invention will be most suitable when the formation of higher and lower alkanes from feed alkanes (rather than the formation of isomers) is the primary goal.

Example II

This example illustrates the effects of the relative amounts of the various catalyst components on the performance of the entire catalyst system (comprising alkylaluminum chloride, chloroalkane, solid) in the conversion process of this invention. Two solids were employed: 18–40 mesh Solid B1 (a gamma-alumina, described in Example I) and 40–100 mesh Solid E (an aluminum oxide/phosphate, also described in Example I). All tests were carried out with liquid samples of about 10 mL containing n-pentane as the feed alkane and isobutylaluminum dichloride and carbon tetrachloride as dissolved catalyst components, essentially in accordance with the test procedure described in Example I. The weights of the various catalyst components and pertinent test results (obtained after a reaction time of 3 hours) are summarized in Table II.

TABLE II

| Solid Catalyst Component | Weight (g) of Catalyst Component | | | Weight Ratio of (i-BuAlCl$_2$ + CCl$_4$) to Solid | n-Pentane Conversion (%) | % Selectivity to | | |
|---|---|---|---|---|---|---|---|---|
| | Solid | i-BuAlCl$_2$ | CCl$_4$ | | | C$_4$ | C$_6+$ | Isopentane |
| B1 | 0.50* | 0.31* | 0.32* | 1.26:1* | 67.7* | 21.7* | 44.1* | 34.2* |
| " | " | 0.19 | 0.37 | 1.12:1 | 4.8 | — | — | — |
| " | " | " | 0.19 | 0.76:1 | 3.6 | — | — | — |
| " | " | " | 0.09 | 0.56:1 | 2.2 | — | — | — |
| " | " | " | 0.02 | 0.42:1 | 1.6 | — | — | — |
| B1 | 0.10 | 0.19 | 0.19 | 2.09:1 | 25.2 | 28.8 | 28.5 | 42.6 |
| " | 0.25 | " | " | 1.52:1 | 27.3 | 25.9 | 27.4 | 46.7 |
| " | 0.50 | " | " | 0.76:1 | 3.6 | — | — | — |
| " | 0.75 | " | " | 0.51:1 | 1.3 | — | — | — |
| " | 1.00 | " | " | 0.38:1 | 1.2 | — | — | — |
| E | 0.50 | 0.25 | 0.26 | 1.02:1 | 52.4 | 26.7 | 28.7 | 44.6 |
| " | " | 0.19 | 0.19 | 0.76:1 | 49.1 | 16.2 | 41.2 | 42.5 |
| " | " | 0.13 | 0.13 | 0.52:1 | 9.1 | — | — | — |
| " | " | 0.09 | 0.10 | 0.38:1 | 4.0 | — | — | — |
| " | " | 0.06 | 0.06 | 0.24:1 | 1.2 | — | — | — |

*Test data from Table I

Test data in Table II indicate that a minimum ratio of the combined weight of the two dissolved catalyst components (isobutylaluminum dichloride and carbon tetrachloride) to the weight of the solid component is required for the catalyst system to be sufficiently active for the conversion of n-pentane. In batch processes employing alumina (Solid 1), this minimum weight ratio was about 1.2:1, whereas in batch processes employing aluminum oxide/phosphate (Solid E), this minimum weight ratio was about 0.8:1. A weight ratio of (isobutylaluminum dichloride +CCl$_4$) to solid of about 1.2:1 or higher is considered adequate for all tested solids in batch reactions (based on the test results in Example I).

Example III

In this example, continuous flow reactor tests for disproportionating n-pentane in accordance with this invention are described.

12–18 mesh samples of several solids described in Example I were tested in continuous runs. A U-shaped stainless steel reactor: tube (inner diameter: 0.29 inch; total length: 60 inches) was filled with 10 cc of a particular solid alumina material. The reactor was heated to the desired reaction temperature of 50° C. A preheated n-pentane feed containing isobutylaluminum dichloride and carbon tetrachloride was pumped through the packed column of the reactor tube at a feed rate of 60 mL/hour. In all tests, the weight percentage of isobutylaluminum chloride in the liquid feed was 4.9 weight-%, and the weight percentage of CCl$_4$ in the liquid feed was 2.4 weight-%. Concurrently with the liquid feed, hydrogen gas was pumped through the column at a rate of 30 mL/hour providing a reactor pressure of 450 psig. The reactor temperature was 50° C. in all test runs. The exiting product stream was analyzed by means of a gas chromatograph at various time intervals. Pertinent test results are summarized in Table III.

TABLE III

| Solid | Reaction Time (Hr.) | % n-Pentane Conversion | % Selectivity to | | |
|---|---|---|---|---|---|
| | | | C$_4$ | C$_6+$ | Isopentane |
| B1 | 1 | 34.6 | 25.6 | 27.8 | 46.6 |
| " | 2 | 36.2 | 22.4 | 31.4 | 46.1 |
| " | 4 | 35.6 | 24.0 | 29.7 | 46.3 |
| " | 6 | 35.8 | 25.0 | 28.7 | 46.3 |
| " | 8 | 35.5 | 23.8 | 30.3 | 45.9 |
| C2 | 1 | 44.8 | 27.1 | 34.4 | 38.5 |
| " | 2 | 43.6 | 27.1 | 33.8 | 39.0 |
| " | 4 | 43.8 | 27.5 | 33.9 | 38.7 |
| " | 6 | 44.1 | 27.9 | 33.2 | 38.9 |
| " | 8 | 44.6 | 27.3 | 33.6 | 39.1 |
| E | 1 | 55.3 | 27.5 | 39.2 | 33.3 |
| " | 2 | 54.2 | 28.2 | 39.8 | 32.0 |
| " | 4 | 57.5 | 28.0 | 39.5 | 32.6 |
| " | 6 | 56.4 | 27.8 | 39.2 | 33.1 |
| " | 8 | 54.8 | 28.2 | 38.8 | 33.1 |
| H | 1 | 36.7 | 26.3 | 31.5 | 42.3 |
| " | 2 | 37.2 | 26.4 | 31.6 | 42.0 |
| " | 4 | 38.5 | 25.4 | 32.8 | 41.9 |
| " | 6 | 37.4 | 25.7 | 32.1 | 42.2 |
| " | 8 | 38.3 | 26.0 | 32.0 | 42.0 |
| K | 1 | 16.6 | 16.0 | 19.7 | 64.3 |
| " | 2 | 16.8 | 14.5 | 22.2 | 63.3 |
| " | 4 | 17.2 | 14.5 | 22.2 | 63.4 |
| " | 6 | 17.0 | 15.3 | 20.5 | 64.1 |
| " | 8 | 17.2 | 16.8 | 19.2 | 64.0 |

The continuous test results in Table III confirm the operability of the process of this invention (demonstrated by batch test data in Table I). The most effective solid catalyst components in the continuous test series of this example were silica (Solid C2) and aluminum oxide/phosphate (Solid E). With the exception of Solid K (sulfonated styrene-vinylbenzene copolymer ion-exchange resin), the combined selectivity to the disproportionation products (i.e., butanes and $C_6+$alkanes) exceeded the selectivity to the product of the competing isomerization reaction (i.e., isopentane).

Example IV

This example illustrates a preferred embodiment of this invention. Referring to FIG. 1, a continuous process for the conversion of n-pentane, including the recycle of soluble catalyst components and of unconverted n-pentane, is carried out as follows.

A n-pentane feed stream 1 is combined with a recycle stream 3 of unconverted n-pentane and recycled alkylaluminum dichloride (preferably isobutylaluminum dichloride). To the combined stream 5 is added dissolved fresh alkylaluminum dichloride through line 7 at such a rate as to provide the desired concentration of the alkylaluminum dichloride in the resulting process stream 9, which is introduced into a mixing chamber 11 (preferably having static mixing means such as baffles). Also introduced into this mixing chamber is carbon tetrachloride stream 13 at such a rate as to provide the desired concentration of carbon tetrachloride in process stream 15 which is fed to the conversion reactor 17 containing a fixed bed of an effective solid (preferably granular alumina). The flow rate of stream 15 and the temperature/pressure conditions in reactor 17 are chosen so as to maximize the conversion of n-pentane.

Product stream 19 is introduced into a fractionator 20 which affords the separation (by fractional distillation) into various products (isobutane stream 21, n-butane stream 22, isopentane stream 23, hexane stream 24), an unconverted n-pentane stream (described later), carbon tetrachloride stream 25, and a bottoms stream (described later). Carbon tetrachloride stream 25 is introduced into a surge tank 26 from which a $CCl_4$ recycle stream 27 is withdrawn. A fresh $CCl_4$ makeup stream 29 is merged with the $CCl_4$ recycle stream at such a rate as to provide the desired flow rate of carbon tetrachloride stream 13 (described earlier).

Bottoms stream 31 from fractionator 20 which contains $C_7+$ alkanes (heptanes and higher alkanes) and dissolved alkylaluminum dichloride is introduced into a distillation column 33. Most of the $C_7+$ alkanes are withdrawn as an overhead stream 34. Bottoms stream 35 which contains alkylaluminum dichloride (and a small portion of higher alkanes) is combined with stream 37 of unconverted n-pentane (from fractionator 20) in a mixing chamber 39 (preferably having static mixing means such as baffles). The formed mixture of recycle n-pentane and alkylaluminum dichloride is pumped through line 41 into a surge tank 43, from which recycle stream 3 (described earlier) is withdrawn at a desired rate.

Pumps, gauges (such as flow meters and analytical instruments measuring the compositions of various process streams), control valves and other commonly used process equipment are not shown in FIG. 1. They can be selected and operated by skilled chemical engineers without undue experimentation. Also not shown are means for further purifying the various process streams 21-24 and 34, e.g., by passing these streams through adsorbent beds containing activated carbon and the like (so as to remove traces of carbon tetrachloride, alkylaluminum dichloride or other impurities which may be present in these streams).

Reasonable variations, modifications and adaptations for various conditions and reactants can be made within the scope of the disclosure and the appended claims without departing from the scope of this invention.

That which is claimed is:

1. An alkane disproportionation process comprising the steps of:
   (1) mixing a liquid feed which comprises at least one feed alkane containing 4–15 carbon atoms per molecule with at least one alkylaluminum chloride and at least one chloroalkane,
   (2) contacting the mixture obtained in step (1) with a solid material selected from the group consisting of alumina, silica, silica-alumina, clays, zeolites, aluminum phosphate, aluminum oxide/phosphate, aluminum borate, aluminum oxide/borate, aluminum sulfate, aluminum oxide/sulfate, sulfonated styrene polymers and mixtures thereof, at effective disproportionation conditions so as to produce a disproportionation product,
   wherein said disproportionation product comprises said at least one feed alkane at a concentration which is lower than the concentration of said at least one feed alkane in said feed,
   wherein said disproportionation product contains at least one higher-boiling, alkane containing more carbon atoms per molecule than said feed alkane and at least one lower-boiling alkane containing fewer carbon atoms per molecule than said feed,
   and wherein the concentrations of said at least higher-boiling alkane and of said at least one lower-boiling alkane are higher in said disproportionation product than in said feed; and
   (3) recovering said at least one higher-boiling alkane and saint at least one lower-boiling alkane from said disproportionation product.

2. A process in accordance with claim 1, wherein said at least one alkylaluminum chloride has the general formula of $R_xAlCl_{3-x}$, wherein x is 1 or 2, and each R is independently selected from the group consisting of alkyl radicals consisting of ethyl, n-propyl, isopropyl, n-butyl, isobutyl, t-butyl, n-pentyl and branched pentyl radicals.

3. A process in accordance with claim 2, wherein said at least one chloroalkane is selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane.

4. An alkane conversion process comprising the steps of:
   (1) mixing a liquid feed which comprises at least one feed alkane containing 4–8 carbon atoms per molecule with at least one alkylaluminum chloride having the general formula of $R_xAlCl_{3-x}$, wherein x is 1 or 2, and each R is independently selected from the group consisting of alkyl radicals consisting of methyl, ethyl, n-propyl, isopropyl, n-butyl, isobutyl, t-butyl, n-pentyl and branched pentyl radicals, and said at least one chloroalkane is selected from the group consisting of dichloromethane, chloroform, carbon tetrachloride, 1,1-dichloroethane, 1,2-dichloroethane, 1,1,1-trichloroethane, 1,1-dichloropropane, 2,2-dichloropropane, 1-chlorobutane and 2-chloro-2-methylbutane;

(2) contacting the mixture obtained in step (1) with a solid material selected from the group consisting of alumina, silica, silica-alumina, clays, zeolites, aluminum phosphate, aluminum oxide/phosphate, aluminum borate, aluminum oxide/borate, aluminum sulfate, aluminum oxide/sulfate, sulfonated styrene-divinylbenzene copolymers and mixtures thereof, at effective disproportionation conditions so as to produce a disproportionation product, wherein said disproportionation product comprises said at least one feed alkane at a concentration which is lower than the concentration of said at least one feed alkane in said feed, wherein said disproportionation product contains at least one higher-boiling alkane containing more carbon atoms per molecule than said feed alkane and at least one lower-boiling alkane containing fewer carbon atoms per molecule than said feed, and wherein the concentrations of said at least one higher-boiling alkane and of said at least one lower-boiling alkane are higher in said disproportionation product than in said feed; and (3) recovering said at least one higher-boiling alkane and said at least one lower-boiling alkane from said disproportionation product.

5. A process in accordance with claim 4, wherein said at least one alkylaluminum chloride is isobutylaluminum dichloride, and said at least one chloroalkane is carbon tetrachloride.

6. A process in accordance with claim 5, wherein said at least one feed alkane is n-pentane.

7. A process in accordance with claim 4, wherein the weight percentage of said at least one alkylaluminum chloride and the weight percentage of said at least one chloroalkane in said liquid feed are about 2-6 weight percent of each.

8. A process in accordance with claim 7, wherein the weight ratio of said at least one alkylaluminum chloride to said at least one chloroalkane in the mixture obtained in step (1) is about 0.5:1 to about 3:1.

9. A process in accordance with claim 8, wherein said at least one alkylaluminum chloride is isobutylaluminum dichloride, and said at least one chloroalkane is carbon tetrachloride.

10. A process in accordance with claim 9, wherein said at least one feed alkane is n-pentane.

11. A process in accordance with claim 8, wherein the ratio of the combined weight of said at least one alkylaluminum chloride and said at least one chloroalkane to said solid material in step (2) is about 1.2:1 to about 2:1.

12. A process in accordance with claim 11, wherein said at least one alkylaluminum chloride is isobutylaluminum dichloride, and said at least one chloroalkane is carbon tetrachloride.

13. A process in accordance with claim 12, wherein said at least one feed alkane is n-pentane.

14. A process in accordance with claim 4, wherein the liquid hourly space velocity of said liquid feed in step (2) is about 1-10 cc feed per cc solid material per hour.

15. A process in accordance with claim 14, wherein said at least one alkylaluminum chloride is isobutylaluminum dichloride, and said at least one chloroalkane is carbon tetrachloride.

16. A process in accordance with claim 15, wherein said at least one feed alkane is n-pentane.

17. A process in accordance with claim 4, wherein said contacting conditions in step (2) comprises a reaction temperature of about 20°-50° C. and a contact time of about 5 minutes to about 10 hours.

18. A process in accordance with claim 4, wherein step (3) comprises fractional distillation.

19. A process in accordance with claim 4, wherein said disproportionation product contains at least one unconverted feed alkane, at least one alkylaluminum chloride and at least one chloroalkane, said process comprising the additional steps of separating said at least one unconverted feed alkane, said at least one alkylaluminum chloride and said at least one chloroalkane from said disproportionation product, and thereafter recycling the thus-separated at least one unconverted feed alkane, the thus-separated at least one alkyl aluminum chloride and the thus-separated at least one chloroalkane to step (1).

20. A process in accordance with claim 19, wherein said at least one unconverted feed alkane is n-pentane, said at least one alkylaluminum chloride is isobutylaluminum dichloride, and said at least one chloroalkane is carbon tetrachloride.

* * * * *

UNITED STATES PATENT AND TRADEMARK OFFICE
CERTIFICATE OF CORRECTION

PATENT NO. : 5,414,184

DATED : May 9, 1995

INVENTOR(S) : An-hsiang Wu et al

It is certified that error appears in the above-identified patent and that said Letters Patent is hereby corrected as shown below:

Claim 1, column 10, line 28, delete "," before "alkane".

Claim 1, column 10, line 37, delete "saint" before "at" and insert --- said --- therefor.

Claim 17, column 12, line 25, delete "comprises" and insert --- comprise --- therefor.

Signed and Sealed this

Eighth Day of August, 1995

*Attest:*

BRUCE LEHMAN

*Attesting Officer*     *Commissioner of Patents and Trademarks*